United States Patent [19]
Fakler et al.

[11] Patent Number: 5,900,186
[45] Date of Patent: May 4, 1999

[54] COMPOSITION AND METHOD FOR REDUCING COPPER OXIDE TO METALLIC COPPER

[75] Inventors: John Fakler, Phoenix; Michael Rush, Scottsdale; Scott Campbell, Fountain Hills, all of Ariz.

[73] Assignee: Morton International, Inc., Chicago, Ill.

[21] Appl. No.: 09/030,687

[22] Filed: Feb. 25, 1998

Related U.S. Application Data

[60] Division of application No. 08/627,931, Apr. 3, 1996, Pat. No. 5,753,309, which is a continuation-in-part of application No. 08/574,946, Dec. 19, 1995, Pat. No. 5,721,014.

[51] Int. Cl.$^6$ ..................................... B44C 1/22
[52] U.S. Cl. ..................... 252/79.1; 216/20; 216/34; 216/105
[58] Field of Search ................ 252/79.1; 216/13, 216/20, 34, 105; 427/96

[56] References Cited

U.S. PATENT DOCUMENTS

| | | | |
|---|---|---|---|
| 3,615,737 | 10/1971 | Schneble et al. | 106/1 |
| 3,635,758 | 1/1972 | Schneble et al. | 427/306 |
| 3,637,392 | 1/1972 | Bigelow | 96/108 |
| 3,656,952 | 4/1972 | Miller | 96/48 |
| 3,959,531 | 5/1976 | Schneble et al. | 427/345 |
| 4,255,194 | 3/1981 | Hough et al. | 106/1.24 |
| 4,617,205 | 10/1986 | Darken | 427/305 |
| 4,642,161 | 2/1987 | Akahoshi et al. | 156/630 |
| 5,006,200 | 4/1991 | Chen | 216/105 X |
| 5,403,650 | 4/1995 | Baudrand et al. | 428/209 |
| 5,721,014 | 2/1998 | Fakler et al. | 427/299 |

OTHER PUBLICATIONS

Reexamination Request For U.S. Patent No. 5,750,087, Filed on Aug. 25, 1995—Reexam Control No. 90/005084.

Akahoshi et al., *New Copper Surface Treatment for Polyinride Multilayer Printed Wiring Boards*, Circuit World 14(1) (1987).

Hitachi, Ltd., Technical Publication: *Chemical Reduction Treatment of Copper Oxide: DMAB Method* (undated).

*Primary Examiner*—William Powell

[57] ABSTRACT

A composition for reducing a copper oxide layer to metallic copper so as to facilitate bonding a resin to the metallic copper is disclosed. The composition is an aqueous reducing solution containing a cyclic borane compound. Examples of such cyclic borane compounds include those having nitrogen or sulfur as a ring-forming member, such as morpholine borane, piperidine borane, pyridine borane, piperazine borane, 2,6-Iutidine borane, 4-methylmorpholine borane, and 1,4-oxathiane borane, and also N,N-diethylaniline borane.

23 Claims, No Drawings

5,900,186

COMPOSITION AND METHOD FOR REDUCING COPPER OXIDE TO METALLIC COPPER

REFERENCE TO RELATED DOCUMENTS

This is a divisional application of a previous application filed in the United States Patent and Trademark Office by John T. Fakler, Michael Rush and Scott Campbell on Apr. 3, 1996, of the same title, and assigned Ser. No. 08/627,931, U.S. Pat. No. 5,753,309, which is a continuation-in-part of a previous application filed in the United States Patent and Trademark Office by John T. Fakler, Michael Rush and Scott Campbell on Dec. 19, 1995, of the same title, and assigned U.S. Ser. No. 08/574,946, U.S. Pat. No. 5,721,014.

FIELD OF THE INVENTION

The present invention relates to a composition and method for reducing copper oxide to metallic copper in the fabrication of multilayer printed circuit boards.

BACKGROUND OF THE INVENTION

Successful fabrication of multilayer printed circuit boards requires bonding together of copper and resin layers. However, direct bonding of copper and resin layers does not provide sufficient bonding strength. Therefore, it is common to improve copper-resin bonding strength by depositing on the copper surface an oxide layer, such as cuprous oxide, cupric oxide, or the like. Formation of the oxide layer, which turns the pink copper surface a black-brown color, creates minute unevennesses on the copper surface which provide an interlocking effect between the copper surface and resin, thus improving bonding strength.

However, copper oxides are readily hydrolyzed and dissolved upon contact with acid. Because various acid treatments are used in later stages of fabrication of multilayer circuit boards, oxide layer deposition has been problematic at best. Acid attack on the oxide layer is commonly referred to in the industry as "pink ring", because as acid strips the black-brown oxide layer from the surface, a ring of bare pink copper becomes evident.

The problem of vulnerability of the oxide layer to acid was solved by the method described in U.S. Pat. No. 4,642,161 to Akahoshi et al., herein incorporated by reference in its entirety; the Akahoshi et al. patent has been assigned to Hitachi, Ltd. The Akahoshi et al. method is also described in Akahoshi et al., *Circuit World* 14(1) (1987), and in the Hitachi, Ltd. technical publication "The Chemical Reduction Treatment of Copper Oxide, DMAB Method (Technology for the Elimination of Pink Ring", both of which references are herein incorporated by reference in their entireties.

In the Akahoshi et al. method, the copper oxide layer is reduced to metallic copper by means of a reducing solution containing an amine borane compound as the active reducing agent. The minute unevennesses created on the copper surface from oxidation remain following reduction, so that the metallic copper surface produced as a result of the reduction process will form a sufficiently strong bond with a resin. In contrast to cupric oxide and cuprous oxide, which are both soluble in acid, the metallic copper surface resulting from the reduction process, which is the same black-brown color as the oxide layer, has good acid resistance. Therefore by reducing the copper oxide to metallic copper, the acid resistance of the surface or panel is increased, and there is a reduced likelihood of the appearance of "pink ring".

The presently known reducing agents which are capable of reducing cupric oxide to metallic copper are amine boranes represented by the general formula: $BH_3NHRR'$ (wherein R and R' are each a member selected from the group consisting of H, $CH_3$, and $CH_2CH_3$), such as dimethylamine borane (DMAB) and ammonia borane. Because amine boranes are costly to manufacture, they are quite expensive, which results in high operating costs for the reduction process.

Thus, it is clearly desirable to develop an alternative reducing agent which is less expensive than the amine boranes, while ensuring that the metallic copper layer resulting from such an alternative reducing agent has good bonding properties and acid resistance.

SUMMARY OF THE INVENTION

In one embodiment, this invention provides a composition for reducing a copper oxide layer to metallic copper so as to facilitate bonding a resin to the metallic copper. The composition includes an aqueous reducing solution containing a cyclic borane compound. Examples of such cyclic borane compounds include morpholine borane, piperidine borane, pyridine borane, piperazine borane, 2,6-lutidine borane, N,N-diethylaniline borane, 4-methylmorpholine borane, and 1,4-oxathiane borane.

In another embodiment, the present invention provides an improvement to a method of bonding copper and a resin together wherein a copper oxide layer is reduced to metallic copper and the metallic copper is bonded to a resin. The improvement includes reducing the copper oxide layer to metallic copper with an aqueous reducing solution containing a cyclic borane compound.

It is an object of the present invention to provide an alternative reducing agent to the amine boranes used for reducing a copper oxide layer to metallic copper so as to facilitate bonding a resin to the metallic copper.

It is another object of the present invention to decrease operating costs associated with copper oxide reduction processes.

Other objects, advantages, and features of the present invention will become apparent from the following specification.

DETAILED DESCRIPTION OF THE INVENTION

The present specification describes a composition and method for reducing copper oxide to metallic copper in the fabrication of multilayer printed circuit boards.

As previously described, copper oxide reduction is particularly useful in the manufacturing of multi-layer printed circuit boards because formation of the oxide layer, which turns the pink copper surface a black-brown color, creates minute unevennesses on the copper surface which provide an interlocking effect between the copper surface and resin, thus improving bonding strength of the layers. However, because copper oxides are soluble in acid, the oxide layer is vulnerable to acid attack.

The Akahoshi et al. method solved the problem of the acid vulnerability of the oxide layer. According to that method, the copper oxide layer is reduced to metallic copper by means of a reducing solution containing an amine borane compound as the active reducing agent. The minute unevennesses created on the copper surface from oxidation remain following reduction, so that the metallic copper surface produced as a result of the reduction process will form a sufficiently strong bond with a resin, and the metallic copper surface resulting from the reduction process, which is the same black-brown color as the oxide layer, has good acid resistance. Because good acid resistance indicates that the copper oxide layer has been successfully reduced to metallic copper (despite no change in color of the surface), and because such a metallic copper surface retains the minute unevennesses created by the earlier oxidation process, good acid resistance also indicates that the metallic copper surface resulting from the reduction process will have an excellent ability to bond with resins such as those described in the Akahoshi et al. patent. Such resins include epoxy resins, polyimide resins, polyamide resins, polyester resins, phenolic resins, and thermoplastic resins such as polyethylene, polyphenylene sulfide, polyether-imide resins, and fluororesins.

The amine boranes disclosed in the Akahoshi et al method are represented by the general formula: BH3NHRR' wherein R and R' are each a member selected from the group consisting of H, CH$_3$, and CH$_2$CH$_3$, as represented below:

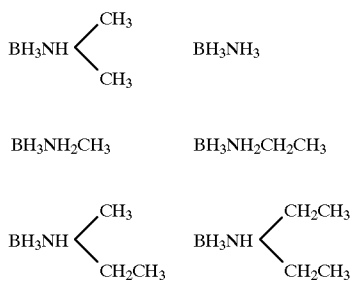

These amine boranes include dimethylamine borane and ammonia borane. However, such amine boranes are expensive; furthermore, after completion of the desired reduction of copper oxide surfaces, the amine boranes are consumed in the reduction solution in amounts greatly in excess of the amount stoichiometrically required for such reduction. Thus, reduction of copper oxide by amine borane compounds typically results in high operating costs.

The present inventor discovered that an aqueous solution containing a cyclic borane, in particular, cyclic borane compounds having nitrogen or sulfur as a ring-forming member, such as the cyclic compound morpholine borane, OC$_4$H$_8$NH:BH$_3$, is very effective in reducing copper oxide to metallic copper so as to facilitate bonding of a resin to the metallic copper in the course of fabrication of multilayer printed circuit boards. The compound morpholine borane contains nitrogen as a ring-forming member, as shown below.

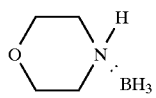

Morpholine borane is less expensive to manufacture than the amine boranes, such as DMAB, presently used in the reduction of copper oxide to metallic copper. The melting point of morpholine borane is 98° (208° F.), compared to DMAB, which has a melting point of 36° (97° F.). Because of its higher melting point, purified morpholine borane can be obtained by distillation at ambient pressure. On the other hand, to purify the lower-melting point compound DMAB, vacuum distillation must be used, resulting in higher manufacturing costs for morpholine borane as compared to DMAB. This relative ease in manufacturing morpholine borane as compared to amine boranes such as DMAB, results in up to a 50% cost savings, thereby significantly decreasing operating costs for the copper oxide reduction process.

The effectiveness of morpholine borane as a reducing agent was determined by processing a copper oxide coated copper panel through a reducing solution containing morpholine borane. Because the metallic copper surface produced from reduction is the same brown-black color as the oxide layer, there are several parameters other than appearance which are measured to test the effectiveness of the reducing process. Such parameters include initiation time, acid resistance, and weight loss of the copper oxide coating after reduction.

The initiation time is the time required for the reduction of the copper oxide to initiate. When the reduction reaction initiates, hydrogen bubbles rapidly form from the copper oxide and continue until the reaction is complete; preferably, initiation occurs within 4 minutes. The acid resistance is determined by immersing the reduced copper in an acid bath. Metallic copper survives longer in acid than do copper oxides; one suggested measure of acid resistance is whether the metallic copper layer can withstand acid resistance for at least about 30 minutes. Thus, the effectiveness of the reduction process can be determined by resistance to acid attack. The weight loss of the panel also determines the effectiveness of the reduction process. A copper oxide panel loses weight when the copper oxide is reduced. By measuring the weight loss of the copper oxide panel, the completeness of reduction can be determined. A low weight loss indicates that the copper oxide is not fully being reduced; preferably, weight loss is greater than 15%. Copper oxide panels were made by growing an oxide layer on a metallic copper panel.

Successful reduction by morpholine borane, as measured by the above parameters, ensures that the minute unevennesses created on the copper surface from oxidation remain following reduction. Those minute unevennesses enable the metallic copper surface produced from morpholine borane reduction to form a sufficiently strong bond with a resin. Such resins include epoxy resins, polyamide resins, phenoloic resins, and thermoplastic resins such as polyethylene, polyphenylene sulfide, polyether-imide resins, and fluororesins. By bonding together copper and resins layers, multilayer printed circuit boards can be successfully fabricated.

The above criteria were used to identify that morpholine borane is effective in reducing copper oxide to metallic copper at concentrations ranging from about 1 g/l to saturation, in order to facilitate bonding a resin to the metallic copper in the fabrication of multilayer printed circuit boards. The preferred morpholine borane concentration is in the range of about 2.7 g/l to 16.8 g/l, in particular, 2.7 g/l. The invention is further described and illustrated with reference to the following examples:

EXAMPLE 1

An aqueous reducing solution was prepared using 1.6 g/L dimethylamine borane and 15.2 g/l sodium hydroxide. The solution, at room temperature, was used as a control to reduce copper oxide formed on the above mentioned copper panels by immersing the panels in the reducing solution for a 4 minute dwell time. The initiation time was recorded. The percent weight loss of the copper oxide coating and the time that the resultant coating survived a 10% by volume hydrochloric acid bath were recorded.

An aqueous reducing solution was prepared using 2.7 g/L morpholine borane and 15.2 g/l sodium hydroxide. This was the experimental formula used to determine the effectiveness of morpholine borane as a reducing agent, and contains the stoichiometric equivalent composition of —$BH_3$ to that contained in a 1.6 g/L DMAB reducing solution. The panels were immersed in the reducing solution for a 4 minute dwell time. The initiation time was recorded. The percent weight loss of the oxide coating and the time that the resultant coating survived a 10% by volume hydrochloric acid bath were recorded.

Both DMAB and morpholine borane were obtained from Aldrich Chemical Company, Milwaukee, Wisconsin. Sodium hydroxide was obtained from Hill Brothers Chemical Company, Orange, Calif.

The results, presented in Table 1, below, indicate that morpholine borane effectively reduces copper oxide to metallic copper.

TABLE 1

| Reducing Agent | Initiation Time | % Weight Loss | Acid Resistance |
| --- | --- | --- | --- |
| Dimethylamine Borane | 26.4 sec | 19.72% | 51.3 min |
| Morpholine Borane | 14.3 sec | 19.77% | 54.5 min |

EXAMPLE 2

The present inventor tested the effectiveness of morpholine borane at other concentrations. The saturation concentration of morpholine borane in an aqueous solution of 15.2 g/l sodium hydroxide in the range of approximately 50 g/l–60 g/l. The results, presented in Table 2, below, indicate that morpholine borane is an effective reducing agent at concentrations ranging from about 1 g/l to saturation.

TABLE 2

| Concentration of Morpholine Borane | Initiation Time | % Weight Loss | Acid Resistance |
| --- | --- | --- | --- |
| 0 g/l | >4 min | <5% | <10 sec |
| 1 g/l | 69 sec | 17% | 45 min |
| 25 g/l | 9 sec | 19% | 50 min |
| 50 g/l | 7 sec | 20% | 50 min |

With respect to the amine borane reducing agents, it is known that the amine boranes continue to be consumed even after all of the cupric oxide on the panels has been reduced to copper metal, and no additional cupric oxide is introduced into the solution. Consumption of the amine boranes continues after reduction of the copper oxide panels because, it is theorized, the reduced copper oxide from the panels is still present in the reducing solution, and may be reoxidized or may catalyze the hydrolysis of the amineboranes. Therefore, the amine boranes are consumed in greater than the stoichiometric amount necessary to reduce the copper oxide on the panels. The excessive consumption of the reducing agent shortens the usable lifetime of the reducing solution, and ultimately results in higher operating costs for the process.

In a co-pending application, the present inventor discloses that addition of reduction stabilizers to amine borane reducing solutions decreased amine borane consumption to between about 11% to 92% of amine borane consumption observed in the absence of such stabilizers. Suitable reduction stabilizers disclosed in the co-pending application include thio-containing (—C(=S)$NH_2$) compounds such as thiourea, triazole-containing ($C_2H_3N_3$) compounds such as tolytriazole and benzotriazole, isoxazole-containing (—$C_3$HNO) compounds such as 3-amino-5-methylisoxazole, thiazole-containing (—NCS—) compounds such as mercaptobenzothiazole, imidazole-containing (—NCN—) compounds such as benzimidazole, and sulfone-containing (—$SO_3$H) compounds such as sulfamic acid.

As described in the co-pending application, the selection of a particular stabilizer and stabilizer concentration is based on several factors, including the following: whether the reduction process stabilized by a given concentration of selected stabilizer is initiated within a reasonable time (preferably in less than about 4 minutes), whether the metallic copper layer resulting from the thus stabilized reduction process is resistant to acid attack (one suggested measure of such resistance is whether the metallic copper layer can withstand acid attack for at least about 30 minutes), and finally, whether the given concentration of selected stabilizer actually results in a decreased consumption of the amine borane reducing agent.

In the co-pending application, with respect to an amine borane solution consisting of 1.6 g/l dimethylamine borane and 15.2 g/l sodium hydroxide at 80° F., the above criteria were used to identify the following preferred stabilizers and effective concentrations: thiourea (about 1 ppm–13 ppm); tolytriazole (about 0.50 ppm); benzotriazole (about 1.0 ppm); 3-amino-5-methylisoxazole (about 100 ppm); mercaptobenzothiazole (about 10 ppm); benzimidazole (about 10 ppm); and sulfamic acid (about 10 g/l). The co-pending application also discloses that increases in reducing agent concentration and temperature can increase the upper limits of effective stabilizer concentrations.

The present inventor discovered that copper oxide reduction by morpholine borane can be similarly stabilized so as to reduce consumption of morpholine borane. The morpholine borane reduction process, stabilized by thiourea, is initiated in a reasonable time and the metallic copper layer resulting from the stabilized reduction process is resistant to acid attack. For example, the present inventor discovered that a reducing solution consisting of 2.7 g/l morpholine borane and 15.2 g/l sodium hydroxide at 80° F. could be stabilized by the addition of thiourea in a concentration in the range of about 2.5 ppm to about 15 ppm.

The present inventor also discovered that, as was the case in his co-pending application, reducing agent concentration and temperature have an effect on the effective concentration range of the stabilizer. For example, in a reducing solution consisting of about 2.7 g/L morpholine borane and 15 g/L sodium hydroxide, raising the temperature from about 80° F. to 120° F. increases the upper limit of the effective concentration range of thiourea stabilizer from about 15 ppm to about 20 ppm. Increasing the morpholine borane concentration to 16.8 g/L, at about 80° F., increases the upper limit of the effective concentration range of thiourea stabilizer to about 160 ppm; at a morpholine borane concentration of 16.8 g/L, if the temperature is increased to 120° F., the upper limit of the effective concentration range of thiourea stabilizer increases to about 200 ppm.

General Procedures for Testing Stabilizers

In order to test the potential stabilizer, the present inventor created reducing solutions similar to those used in an actual copper oxide reduction process. The reducing solutions were then poisoned with copper oxide, because during an actual copper oxide reduction process, copper oxide remains in the reducing solution after the reduced copper panels are removed. The remaining copper oxide consumes further amounts of the reducing agent, resulting in overall consumption of reducing agent in greater than the stoichiometric amount necessary for reduction of copper oxide on the panels. Thus, the consumption of reducing agent per gram of copper oxide and the consumption of reducing agent per time could be determined. The concentration of the reducing agent was analytically determined initially and after 24 hours, via iodometric titration.

The possible negative effects the potential stabilizer could have on the copper oxide reduction process were determined by processing a copper oxide panel through the reducing solution containing a given potential stabilizer. As described above, there were several parameters examined to determine the effectiveness of such stabilized reducing processes; reduction process initiation time, acid resistance of the metallized copper surfaces resulting from the stabilized reduction, and weight loss of the copper oxide coating after reduction.

Initiation time is the time required for copper oxide reduction to begin. When the reduction reaction begins, hydrogen bubbles rapidly form and continue until the reaction is complete. Acid resistance was determined by immersing the resulting metallized copper surface in an acid bath. Metallic copper survives longer than copper oxides in an acid bath. Thus, the effectiveness of a given stabilized reduction process in producing the desired metallic copper surface, was determined by resistance to acid attack.

Weight loss of the tested panel also determines the effectiveness of the reduction process. Copper oxide loses weight when it is chemically reduced to copper metal. By measuring the weight loss of the panels, the completeness of reduction was determined. A low weight loss indicates that the copper oxide is not fully being reduced. Copper oxide panels were made by growing an oxide layer on a metallic copper panel.

EXAMPLE 3

To test the effect of the potential reducing stabilizer thiourea, an aqueous reducing solution was prepared using 2.7 grams per liter morpholine borane and 15.2 g/L sodium hydroxide. DMAB was obtained from Aldrich Chemical Company, Milwaukee, Wis. Sodium hydroxide was obtained from Hill Brothers Chemical Company, Orange, Calif. That solution, at room temperature, was used as the control solution. An experimental solution was prepared by adding 2.5 ppm of thiourea to a solution identical in composition to the control solution. Both the control and the experimental solutions were poisoned with 0.075 g/L of copper oxide. The concentration of morpholine borane in both solutions was analyzed before the copper oxide was added, and 24 hours after the copper oxide was added. The results are provided in Table 3.

TABLE 3

| Morpholine Borane Solution | Initial Concent. Morpholine Borane | Stoichio. Consump. of Morpholine Borane to Reduce All Copper Oxide | Consumption of Morpholine Borane Over 24 Hours |
| --- | --- | --- | --- |
| Control | 2.70 g/L | 0.0317 g/L | 1.1745 g/L |
| Experimental | 2.70 g/L | 0.0317 g/L | 0.2784 g/L |

EXAMPLE 4

The effective stabilization range of thiourea for morpholine borane was tested to a solution of 2.7 g/L morpholine borane and 15.2 g/L sodium hydroxide, thiourea was added at 5 ppm intervals, and the solution's ability to reduce copper oxide and stability were determined. The measured parameters were initiation time, percent weight loss, acid resistance, and consumption over 24 hours. The results are presented in Table 4.

TABLE 4

| Concent. of Thiourea | Initiation Time | % Weight Loss | Acid Resistance | Consump. of Morpholine Borane Over 24 Hours |
| --- | --- | --- | --- | --- |
| 0 ppm | 25 sec | 20% | 40 min | 1.78 g/L |
| 5 ppm | 30 sec | 20% | 40 min | 0.25 g/L |
| 10 ppm | 30 sec | 18% | 45 min | 0.19 g/L |
| 15 ppm | 40 sec | 16% | 35 min | 0.14 g/L |
| 20 ppm | 60 sec | 9% | <1 min | 0.11 g/L |

The above results indicate that in a 2.7 g/L morpholine borane solution, thiourea can be added to a concentration up to about 15 ppm, and good copper reduction can be achieved. Also evident from the above data is the fact that the more thiourea added to the reducing solution, the less morpholine borane is consumed.

EXAMPLE 5

In this example, the concentrations of both morpholine borane and thiourea were varied. Reducing solutions of (1) 8.4 g/L MB, 15.2 g/L sodium hydroxide, and (2) 16.8 g/L MB, 1.2 g/L sodium hydroxide were made. Thiourea was added over the side of the reducing baths, and the reduction of copper oxide panels was determined. The measured parameters were initiation time, percent weight loss, and acid resistance. The results are presented in Table 5

TABLE 5

| Concent. of MB | Thiourea Concent. | Initiation Time | % Weight Loss | Acid Resistance |
| --- | --- | --- | --- | --- |
| 8.4 g/L | 0 ppm | 10 sec | 21.3% | 50 min |
| 8.4 g/L | 10 ppm | 10 sec | 18.7% | 50 min |
| 8.4 g/L | 20 ppm | 15 sec | 20.9% | 50 min |
| 8.4 g/L | 30 ppm | 15 sec | 16.5% | 50 min |
| 8.4 g/L | 40 ppm | 15 sec | 18.3% | 45 min |
| 8.4 g/L | 50 ppm | 20 sec | 16.1% | 50 min |
| 8.4 g/L | 60 ppm | 25 sec | 15.8% | 45 min |
| 8.4 g/L | 70 ppm | 25 sec | 15.7% | <1 min |
| 16.8 g/L | 0 ppm | 5 sec | 22.8% | 50 min |
| 16.8 g/L | 25 ppm | 5 sec | 17.6% | 50 min |
| 16.8 g/L | 50 ppm | 10 sec | 16.1% | 50 min |
| 16.8 g/L | 75 ppm | 10 sec | 19.7% | 50 min |
| 16.8 g/L | 100 ppm | 10 sec | 18.3% | 45 min |
| 16.8 g/L | 120 ppm | 15 sec | 17.5% | 45 min |
| 16.8 g/L | 140 ppm | 15 sec | 17.1% | 50 min |
| 16.8 g/L | 160 ppm | 15 sec | 16.8% | 50 min |
| 16.8 g/L | 180 ppm | 15 sec | 16.4% | <1 min |

These results indicate that thiourea may be used as a stabilizer in a morpholine borane reducing solution at concentrations ranging from greater than 0 ppm thiourea to 160 ppm. Based on the trends evident from these results, it is probable that reducing solutions of morpholine borane having concentrations greater than 16.8 g/L MB may still use thiourea as a stabilizer at concentrations greater than 160 ppm thiourea.

EXAMPLE 6

As seen in Example 5, Table 5, the effective concentration range of stabilizer in the reducing solution is dependent on the concentration of reducing agent. The effective concentration range of stabilizer in the reducing solution is also dependent on the temperature of the reducing solution.

To illustrate the effects of temperature on a morpholine borane reducing solution with thiourea as a stabilizer, reducing solutions of similar morpholine borane concentrations and thiourea concentrations were made and the ability to reduce copper oxide panels at various temperatures were tested.

An aqueous solution of 2.7 grams per liter dimethylamine borane, 15.2 g/L sodium hydroxide, and 20 ppm thiourea was made. The solution's ability to reduce copper oxide panels was determined for several temperatures. The results are listed in Table 6 below.

TABLE 6

| Morpholine Borane Concentration | Thiourea Concentration | Temperature | % Weight Loss | Initiation Time | Acid Resistance |
|---|---|---|---|---|---|
| 2.7 g/L | 20 ppm | 80° F. | 9.0 | 60 sec | <1 min |
| 2.7 g/L | 20 ppm | 100° F. | 15.6 | 45 sec | 35 min |
| 2.7 g/L | 20 ppm | 120° F. | 19.8 | 40 sec | 40 min |

An aqueous solution of 8.4 grams per liter morpholine borane, 15.2 g/L sodium hydroxide and 70 ppm thiourea was made. The solution's ability to reduce copper oxide panels was determined at several temperatures. The results are listed in Table 7 below.

TABLE 7

| Morpholine Borane Concentration | Thiourea Concentration | Temperature | % Weight Loss | Initiation Time | Acid Resistance |
|---|---|---|---|---|---|
| 8.4 g/L | 70 ppm | 80° F. | 15.7 | 25 sec | <1 min |
| 8.4 g/L | 70 ppm | 100° F. | 18.1 | 25 sec | 35 min |
| 8.4 g/L | 70 ppm | 120° F. | 19.3 | 20 sec | 40 min |

An aqueous solution of 16.8 grams per liter morpholine borane, 15.2 g/L sodium hydroxide and 200 ppm thiourea was made. The solutions ability to reduce copper oxide panels was determined at several temperatures. The results are listed in Table 8 below.

TABLE 8

| Morpholine Borane Concentration | Thiourea Concentration | Temperature | % Weight Loss | Initiation Time | Acid Resistance |
|---|---|---|---|---|---|
| 16.8 g/L | 200 ppm | 80° F. | 15.1 | 20 sec | <1 min |
| 16.8 g/L | 200 ppm | 100° F. | 17.0 | 15 sec | 35 min |
| 16.8 g/L | 200 ppm | 120° F. | 18.8 | 15 sec | 40 min |

The present inventor also discovered an additional improvement to the reduction process which can be realized by using morpholine borane instead of alkane boranes. Morpholine borane stabilized with thiourea shows more stability after the reducing bath has been continuously processed and replenished than a comparable DMAB reducing solution stabilized with thiourea which has been continuously processed and replenished.

This improvement can be explained by examining and comparing the DMAB and morpholine borane reduction processes more closely. In DMAB reduction, a reducing bath containing 1.5 g/L DMAB and 15.2 g/L NaOH is initially made. Copper oxide panels are then processed through the reducing bath. The copper oxide is reduced by the dimethylamine borane. In the reaction, the boron atom in the DMAB is oxidized and the copper oxide is reduced. It is believed that the dimethylamine functional group is left as a side product.

The typical concentration of DMAB used for reducing copper oxide panels is 1.6 g/L DMAB. Therefore, an automatic control system is set up to replenish the DMAB and keep a constant concentration of 1.6 g/L DMAB. As replenishment continues, the dimethylamine side product accumulates in the tank. Therefore, a constant concentration of DMAB is present in the reducing solution, 1.6 g/L DMAB, but the concentration of the dimethylamine functional group is continuously increasing.

The concentration of the dimethylamine functional group reaches an equilibrium when the amount of the dimethylamine functional group being formed is equivalent to the amount of dimethylamine being dragged out of the reducing solution on the panels. (It is a rough estimate that 10–15 mL of reducing solution per square foot of panel is dragged out of the reducing solution tank.)

Therefore, after a period of replenishment, the process should finally be in equilibrium with respect to the dimethylamine functional group. That is there should be 1.6 g/L DMAB, 15.2 g/L NaOH, and probably a constant concentration of dimethylamine functional group side product, and probably a constant concentration of a boron containing side product resulting from the reduction process. This more accurately represents the reducing bath as it will be run in the process.

In summary, there are two main states of the bath, initial and at equilibrium. The parameters of % weight loss, acid resistance, initiation time, consumption over ½ turnover, and consumption over 24 hours were tested. The bath is initially made up of 1.6 g/L DMAB and 15.2 g/L NaOH. To mimic equilibrium, which is reached in approximately 20 days, copper oxide is added to the initial bath to decrease the concentration of DMAB in half over 24 hours. This is continued until the DMAB is replenished 20 times. The sum total of the 20 replenishments of ½ the initial concentration has been designated "10 turnovers," an initial bath is designated "zero turnovers." After 10 turnovers, the reducing solution now has roughly an equilibrium amount of dimethylamine side products together with 1.6 g/L DMAB and 15.2 g/L NaOH. Note that this does not precisely mimic an actual process, because in an actual process, DMAB is continuously replenished to maintain the DMAB level constant at 1.6 g/L DMAB, while the concentration of dimethylamine side product increases to the equilibrium amount, i.e. the controller does not let half of the DMAB present react before replenishment is made.

The above scenario is similar for morpholine borane, MB. The initial concentration of morpholine borane is 2.7 g/L MB and 15.2 g/L NaOH. Side product formed during the reduction of copper oxide is probably the morpholine complex. As the morpholine borane is replenished during the reduction process, the morpholine borane remains at a constant concentration of 2.7 g/L MB, but the concentration of the suspected side product, the morpholine complex, continues to increase until the bath reaches equilibrium with respect to the morpholine complex. Testing for the same parameters as was done above with respect to DMAB was done initially and after 20 replenishments of morpholine borane. As above, half of the morpholine borane was consumed and added back, and again the sum total of the 20 replenishments of ½ the initial concentration was designated 10 turnovers; the initial bath was designated zero turnovers.

The above discussion described the process without addition of the stabilizer thiourea. When thiourea is used to stabilize the reduction, the stabilizer is added back with the DMAB or the morpholine borane, depending on which reducing agent is used. For example, the concentration of thiourea is initially 2.5 ppm, then the actual concentration of thiourea starts at 2.5 ppm and increases with each replenishment of DMAB or morpholine borane, as the case may be, until equilibrium is reached.

The results presented in Table 9 illustrate the excellent benefits of using MB as opposed to DMAB. When stabilizing a DMAB reducing solution with thiourea, the consumption over 24 hours greater than doubles after 10 turnovers, compared to the initial consumption over 24 hours at zero turnovers (compare row 8 to row 2, and row 9 to row 3). In contrast, when using morpholine borane stabilized by thiourea, the consumption over 24 hours does not double, but only increases by 20–30% of the original consumption over 24 hours at zero turnovers (compare row 11 to row 5, and row 12 to row 6).

TABLE 9

10 Turnover (TO) Results: DMAB and Morpholine Borane
(with and without Thiourea)
Initial DMAB concentration: 1.6 g/L
Initial Morpholine Borane concentration: 2.7 g/L

| Reduction solution comp. | % Wt. Loss | Init. Time | Acid Resist. | Consum. over 24 hrs.* (% consum. 24 hrs.) |
|---|---|---|---|---|
| At Zero Turnovers: | | | | |
| Row 1 | | | | |
| DMAB 0.0 ppm Thiourea | 20.8% | 29.3 sec | 50.1 min | 12.1 (42.3%) |
| Row 2 | | | | |
| DMAB 2.5 ppm Thiourea | 21.3% | 30.7 sec | 50.0 min | 2.27 (8.06%) |
| Row 3 | | | | |
| DMAB 5.0 ppm Thiourea | 20.0% | 38.1 sec | 48.4 min | 1.61 (5.76%) |
| Row 4 | | | | |
| Morpholine Borane 0.0 ppm Thiourea | 20.6% | 18.2 sec | 37.6 min | 12.4 (43.8%) |
| Row 5 | | | | |
| Morpholine Borane 2.5 ppm Thiourea | 23.2% | 20.0 sec | 48.1 min | 2.92 (10.6%) |
| Row 6 | | | | |
| Morpholine Borane 5.0 ppm Thiourea | 20.6% | 26.1 sec | 45.7 min | 2.17 (7.96%) |

TABLE 9-continued

10 Turnover (TO) Results: DMAB and Morpholine Borane
(with and without Thiourea)
Initial DMAB concentration: 1.6 g/L
Initial Morpholine Borane concentration: 2.7 g/L

| Reduction solution comp. | % Wt. Loss | Init. Time | Acid Resist. | Consum. over 24 hrs.* (% consum. 24 hrs.) |
|---|---|---|---|---|
| At 10 Turnovers: | | | | |
| Row 7 | | | | |
| DMAB 0.0 ppm Thiourea | 18.6% | 36.3 sec | 45.6 min | 14.7 (58.4%) |
| Row 8 | | | | |
| DMAB 2.5 ppm Thiourea | 18.1% | 41.1 sec | 44.4 min | 4.85 (19.6%) |
| Row 9 | | | | |
| DMAB 5.0 ppm Thiourea | 17.1% | 46.8 sec | 42.0 min | 3.07 (11.8%) |
| Row 10 | | | | |
| Morpholine Borane 0.0 ppm Thiourea | 19.5% | 29.3 sec | 40.4 min | 17.1 (66.1%) |
| Row 11 | | | | |
| Morpholine Borane 2.5 ppm Thiourea | 18.2% | 30.7 sec | 38.2 min | 3.31 (12.7%) |
| Row 12 | | | | |
| Morpholine Borane 5.0 ppm Thiourea | 16.2% | 33.2 sec | 39.3 min | 2.51 (9.33%) |

*Consumption over 24 hours is expressed as mol. reducing agent (DMAB or morpholine borane)/mol. copper oxide (add other notes).

The present inventor discovered that there are cyclic borane compounds in addition to morphine borane which are very effective in reducing copper oxide to metallic copper so as to facilitate bonding of a resin to the metallic copper in the course of fabrication of multilayer printed circuit boards. The cyclic borane compounds include piperidine borane, pyridine borane, piperazine borane, 2,6-Iutidine borane, 4-ethylmorpholine borane, N,N-diethylaniline borane, 4-methylmorpholine borane, and 1,4-oxathiane borane. As can be seen by referring to the structures of these compounds set forth below, as with morpholine borane, seven of the compounds (in other words, all except N,N-diethylaniline borane) contain nitrogen or sulfur as a ring-forming member.

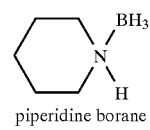
piperidine borane

pyridine borane

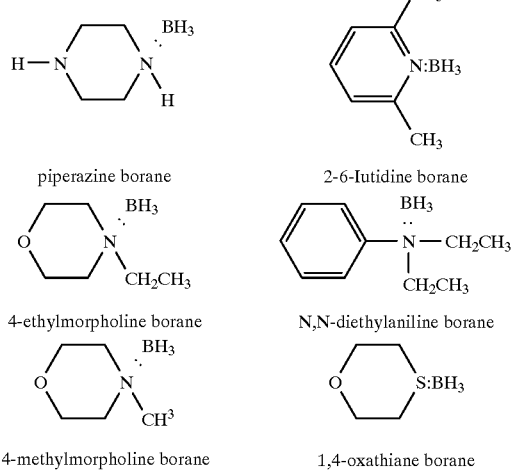

piperazine borane
2-6-Iutidine borane
4-ethylmorpholine borane
N,N-diethylaniline borane
4-methylmorpholine borane
1,4-oxathiane borane The effectiveness of the above cyclic borane compounds as reducing agents was determined by processing a copper oxide coated copper panel through a reducing solution containing the cyclic borane compound. Because the metallic copper surface produced from reduction is the same brown-black color as the oxide layer, there were several parameters other than appearance which were measured to test the effectiveness of the reducing process. Such parameters included initiation time, acid resistance, and weight loss of the copper oxide coating after reduction.

The initiation time is the time required for the reduction of the copper oxide to initiate. When the reduction reaction initiates, hydrogen bubbles rapidly form from the copper oxide and continue until the reaction is complete; preferably, initiation occurs within 4 minutes. The acid resistance was determined by immersing the reduced copper in an acid bath. Metallic copper survives longer in acid than do copper oxides; one suggested measure of acid resistance is whether the metallic copper layer can withstand acid resistance for at least about 30 minutes. Thus, the effectiveness of the reduction process can be determined by resistance to acid attack. The weight loss of the panel also determines the effectiveness of the reduction process. A copper oxide panel loses weight when the copper oxide is reduced. By measuring the weight loss indicates that the copper oxide is not fully being reduced; preferably, weight loss is greater than 15%. Copper oxide panels were made by growing an oxide layer on a metallic copper panel.

Successful reduction by the cyclic borane compounds, as measured by the above parameters, ensures that the minute unevenness created on the copper surface from oxidation remain following reduction. Those minute unevenness enable the metallic copper surface produced from the cyclic borane compound reduction to form a sufficiently strong bond with a resin. Such resins include epoxy resins, polyamide resins, phenoloic resins, and thermoplastic resins such as polyethylene, polyphenylene sulfide, polyether-imide resins, and fluorocesins. By bonding together copper and resins layers, multilayer printed circuit boards can be successfully fabricated.

The above criteria were used to identify which borane compounds were effective in reducing copper oxide, in order to facilitate bonding a resin to the metallic copper in the fabrication of multilayer printed circuit boards. The invention is further described and illustrated with reference to the following examples:

EXAMPLE 7

An aqueous reducing solution was prepared using 25 g/L dimethylamine borane. The solution, at room temperature, was used as a control to reduce copper oxide formed on the above-mentioned copper panels by immersing the panels in the reducing solution for a 4-minute dwell time. The initiation time was recorded. The percent weight loss of the copper oxide coating and the time that the resultant coating survived a 10% by volume hydrochloric acid bath were recorded.

An aqueous reducing solution was prepared using 42 g/L piperidine borane. This was the experimental formula used to determine the effectiveness of piperidine borane as a reducing agent, and contains the stoichiometric equivalent composition of —$BH_3$ to that contained in the control solution, a 25 g/L DMAB reducing solution. The panels were immersed in the reducing solution for a 4-minute dwell time. The initiation time was recorded. The percent weight loss of the oxide coating and the time that the resultant coating survived a 10% by volume hydrochloric acid bath were recorded.

Both DMAB and piperidine borane were obtained from Aldrich Chemical Company, Milwaukee, Wis.

The results, presented in Table 10, below, indicate that piperidine borane effectively reduces copper oxide to metallic copper.

TABLE 10

| Reducing Agent | Initiation Time | % Weight Loss | Acid Resistance |
| --- | --- | --- | --- |
| Dimethylamine Borane | 26 sec | 19.7% | 51 min |
| Piperidine Borane | 4 sec | 17.9% | 35 min |

EXAMPLE 8

An aqueous reducing solution was prepared using 25 g/L dimethylamine borane. The solution, at room temperature, was used as a control to reduce copper oxide formed on the above-mentioned copper panels by immersing the panels in the reducing solution for a 4-minute dwell time. The initiation time was recorded. The percent weight loss of the copper oxide coating and the time that the resultant coating survived a 10% by volume hydrochloric acid bath were recorded.

Aqueous solutions of each experimental borane compound were made, containing the stoichiometric equivalent composition of —$BH_3$ to that contained in the control, a 25 g/L DMAB reducing solution. The experimental borane compounds included morpholine borane, piperidine borane, pyridine borane, piperazine borane, 2,6-iutidine borane, 4-ethylmorpholine borane, N,N-diethylanaline borane, 4-methylmorpholine borane, and 1,4-oxathiane borane. The panels were immersed in the reducing solution for a 4-minute dwell time. The initiation time was recorded. The percent weight loss of the oxide coating and the time that the resultant coating survived a 10% by volume hydrochloric acid bath were recorded.

All of the above borane compounds were obtained from Aldrich Chemical Company, Milwaukee, Wis.

The results, presented in Table 11, below, indicate that the cyclic borane compounds effectively reduce copper oxide to metallic copper.

TABLE 11

| Borane Compound, Concentration | Initiation Time | % Weight Loss | Acid Resistance |
|---|---|---|---|
| Dimethylamine Borane, 25 g/L | 26 sec | 19.18% | 51 min |
| Morpholine Borane, 42 g/L | 14 sec | 19.7% | 55 min |
| Piperidine Borane, 42 g/L | 40 sec | 17.9% | 35 min |
| Pyridine Borane, 39 g/L | 60 sec | 16.7% | 30 min |
| Piperazine Borane, 42 g/L | 20 sec | 18.9% | 45 min |
| 2,6-Iutidine Borane, 51 g/L | 10 sec | 15.5% | 30 min |
| 4-Ethylmorpholine Borane, 55 g/L | 40 sec | 17.7% | 40 min |
| N,N-Diethylaniline Borane, 69 g/L | 5 sec | 17.0% | 50 min |
| 4-Methylmorpholine Borane, 48 g/L | 10 sec | 17.7% | 35 min |
| 1,4-Oxathiane Borane, 60 g/L | 5 sec | 17.3% | 30 min |

EXAMPLE 9

(Prophetic)

Based on observations made by the present inventor with respect to the effectiveness ranges (about 1.0 g/L to saturation) of morpholine borane for reducing copper oxide to metallic copper on the observed data for the other cyclic borane, and on comparisons of the structure of morpholine borane with the structures of the other cyclic boranes, the present inventor expects that the ranges of concentrations for which the cyclic boranes will be effective in reducing copper oxide to metallic copper will be as follows:
piperidine borane: about 1.0 g/L to saturation
pyridine borane: about 0.9 g/L to saturation
piperazine borane: about 1.0 g/L to saturation
2,6-Iutidine borane: about 1.2 g/L to saturation
4-ethylmorpholine borane: about 1.3 g/L to saturation
N,N-diethylaniline borane: about 1.3 g/L to saturation
4-methylmorphine borane: about 1.1 g/L to saturation
1,4-oxathiane borane: about 1.2 g/L to saturation

EXAMPLE 10

(Prophetic)

The procedures followed in the General Procedures for Testing Stabilizers and in Examples 3–6 will be used, except that the following cyclic boranes will be substituted for morpholine borane in respective testings of each cyclic borane:
piperidine borane
pyridine borane
piperazine borane
2,6-Iutidine borane
N,N-diethylaniline borane
4-methylmorpholine borane
1,4-oxathiane borane Based on observations made by the present inventor as to the stabling effect thiourea has on morpholine borane reduction, and on comparisons of the structure of morpholine borane with the structures of the other cyclic boranes, the present inventor expects that the consumption of the other cyclic boranes will be decreased in a similar manner to the decreased morpholine borane consumption observed in Examples 3–6, when the reducing stabilizer thiourea is present in the reducing solution at a concentration in the range of about 2.5 ppm to 200 ppm.

It is to be understood that the present invention is not confined to the particular construction and arrangement herein illustrated and described, but embraces such modified forms thereof as comes within the scope of the following claims.

What is claimed is:

1. A composition for reducing a copper oxide layer to metallic copper so as to facilitate bonding a resin to the metallic copper, the composition comprising an aqueous reducing solution containing a cyclic borane compound.

2. The composition of claim 1, wherein the cyclic borane compound is selected from the group consisting of cyclic borane compounds having nitrogen as a ring-forming member, cyclic borane compounds having sulfur as a ring-forming member, and N,N-diethylaniline borane.

3. The composition of claim 2, wherein the cyclic borane compound is morpholine borane.

4. The composition of claim 3, wherein the morpholine borane is present at a concentration in the range of about 1.0 g/l to saturation.

5. The composition of claim 4, wherein the morpholine borane is present at a concentration in the range of about 2.7 g/l to 16.8 g/l.

6. The composition of claim 2, wherein the cyclic borane compound is piperidine borane.

7. The composition of claim 6, wherein the piperidine borane is present at a concentration in the range of about 1.0 g/l to saturation.

8. The composition of claim 2, wherein the cyclic borane compound is pyridine borane.

9. The composition of claim 8, wherein the pyridine borane is present at a concentration in the range of about 0.9 g/l to saturation.

10. The composition of claim 2, wherein the cyclic borane compound is piperazine borane.

11. The composition of claim 10, wherein the piperazine borane is present at a concentration in the range of about 1.0 g/l to saturation.

12. The composition of claim 2, wherein the cyclic borane compound is 2,6 Iutidine borane.

13. The composition of claim 12, wherein the 2,6 Iutidine borane is present at a concentration in the range of about 1.2 g/l to saturation.

14. The composition of claim 2, wherein the cyclic borane compound is 4-ethylmorpholine borane.

15. The composition of claim 14, wherein the 4-ethylmorpholine borane is present at a concentration in the range of about 1.3 g/l to saturation.

16. The composition of claim 2, wherein the cyclic borane compound is 4-methylmorpholine borane.

17. The composition of claim 16, wherein the 4-methylmorpholine borane is present at a concentration in the range of about 1.1 g/l to saturation.

18. The composition of claim 2, wherein the cyclic borane compound is 1,4 oxathiane borane.

19. The composition of claim 18, wherein the 1,4 oxathiane borane is present at a concentration in the range of about 1.2 g/l to saturation.

20. The composition of claim 2, wherein the cyclic borane compound is N,N-diethylaniline borane present at a concentration in the range of about 1.3 g/l to saturation.

21. The composition of claim 2, further comprising a reducing stabilizer in an amount sufficient to decrease consumption of the cyclic borane compound during reduction to a level less than that consumed in the absence of the reducing stabilizer during the course of a copper oxide reduction process, wherein the stabilized reduction process is initiated in a reasonable time and the metallic copper layer resulting from the stabilized reduction process is resistant to acid attack.

22. The composition of claim 21, wherein the reducing stabilizer is thiourea.

23. The composition of claim 22, wherein thiourea is present at a concentration in the range of about 2.5 ppm to 200 ppm.

* * * * *